(12) United States Patent
Bara

(10) Patent No.: US 6,342,237 B1
(45) Date of Patent: Jan. 29, 2002

(54) MAKE-UP COMPOSITION COMPRISING FIBERS

(75) Inventor: Isabelle Bara, Paris (FR)

(73) Assignee: L'Oréal, Paris (FR)

( * ) Notice: Subject to any disclaimer, the term of this patent is extended or adjusted under 35 U.S.C. 154(b) by 0 days.

(21) Appl. No.: 09/612,229

(22) Filed: Jul. 7, 2000

(30) Foreign Application Priority Data

Jul. 8, 1999 (FR) .............................. 99 08960

(51) Int. Cl.$^7$ .............................. A61K 7/00; A61K 9/14; A61K 31/08

(52) U.S. Cl. .................. 424/401; 424/484; 424/488; 424/486; 514/772.3; 514/844; 514/845; 514/846; 514/847; 514/848

(58) Field of Search .................. 424/63, 407, 488, 424/484, 486; 514/844, 845, 846, 847, 849, 772.3

(56) References Cited

U.S. PATENT DOCUMENTS 4,992,476 A * 2/1991 Geria .................. 514/782
6,166,093 A * 12/2000 Mougin et al. .......... 514/772.1

FOREIGN PATENT DOCUMENTS

| | | |
|---|---|---|
| EP | 0 100 194 | 2/1984 |
| EP | 0 336 900 | 10/1989 |
| EP | 751162 A1 * | 1/1997 |
| JP | 57-158714 | 9/1982 |
| JP | 7-179323 | 7/1995 |
| JP | 9-263518 | 10/1997 |
| WO | WO 97/29734 | 8/1997 |
| WO | WO-9729734 A1 * | 8/1997 |
| WO | WO 00/06114 | 2/2000 |

OTHER PUBLICATIONS

G. Fonnum et al., "Associative Thickeners. Part I: Synthesis, Rehology and Aggregation Behavior", Colloid & Polymer Science, vol. 271, No. 4, Apr. 1993, pp. 380–389.

Database Chemical Abstracts, XP002133921, JP 07 196440, Aug. 1, 1995.

English language Derwent Abstract of JP 57–158714, Sep. 30, 1982.

English language Derwent Abstract of JP 7–179323, Jul. 18, 1995.

English language Derwent Abstract of JP 9–263518, Oct. 7, 1997.

* cited by examiner

*Primary Examiner*—Thurman K. Page
*Assistant Examiner*—Rachel M. Bennett
(74) *Attorney, Agent, or Firm*—Finnegan, Henderson, Farabow, Garrett, & Dunner, L.L.P.

(57) ABSTRACT

A process for making up or caring for keratin fibers. A cosmetic composition comprising fibers and at least one film-forming polymer in the form of particles in aqueous dispersion is applied to the keratin fibers.

45 Claims, No Drawings

MAKE-UP COMPOSITION COMPRISING FIBERS

The present invention relates to a make-up or care process for the skin, comprising applying to the skin a cosmetic composition comprising fibers and an aqueous dispersion of at least one film-forming polymer. The invention also relates to a cosmetic composition comprising fibers and an aqueous dispersion of at least one film-forming polyurethane polymer. The make-up process and the composition are more particularly intended for making up the body and the facial skin, including the lips, the eyelids, and the ears (and in particular the earlobes) of humans.

Make-up products are commonly used to give color, to accentuate certain parts of the skin or superficial body growths, or alternatively, to give the skin or superficial body growths a glossy, matte, or satin appearance. These products are usually applied in the form of a thin uniform coat. However, when the skin has imperfections such as blemishes, spots, or scars, these imperfections are not well camouflaged on account of the thinness of the make-up, in particular because the relief of these imperfections emerges despite the make-up, and the appearance is therefore not uniform. Moreover, with changes in fashion, more demanding consumers are looking for novel make-up products which give original or particular make-up effects, and, in particular, which impart visible transformations to the made-up face or body.

It is known, for example in document JP-A-7 196 440, to use fibers in a make-up composition for the skin to give the skin a velvety feel. However, the fibers in this type of composition do not adhere well to the skin and have a tendency to be removed over time. Such a composition is thus not suitable for providing effective and long-lasting camouflage to skin imperfections.

The aim of the present invention is thus to propose a make-up composition which, at least in some embodiments, gives a make-up which adheres well to the skin and which effectively camouflages skin imperfections.

The inventor has thus discovered that such a make-up can be obtained by using fibers combined with film-forming polymer in aqueous dispersion. In particular, the inventor has obtained make-up embodiments having good staying power, which are, for example, resistant to rubbing and to water. The fibers have good cohesion in the polymer film and thus provide long-lasting camouflage to the imperfections of the made-up skin.

Documents JP-A-57 158 714, JP-A-9 263 518, and JP-A-7 179 323, the disclosures of which are specifically incorporated by reference herein, disclose mascara compositions comprising fibers and an aqueous dispersion of acrylic polymer or of vinyl acetate. However, these documents do not suggest using these compositions for the skin to camouflage its imperfections. In particular, the requirements as regards the film deposited are different: a film formed on the skin or the lips should be able to follow their movements.

Thus, a subject of the present invention is a process for making up or caring for the skin, comprising applying to the skin a cosmetic composition comprising, in a physiologically acceptable medium, fibers and at least one film-forming polymer in the form of particles in aqueous dispersion. Another subject of the invention is a cosmetic composition comprising, in a physiologically acceptable medium, fibers and at least one film-forming polymer in the form of particles in aqueous dispersion, wherein the film-forming polymer is a polyurethane. Another subject of the invention is a process for improving the staying power of a cosmetic composition, comprising adding to the composition fibers and at least one film-forming polymer in the form of particles in aqueous dispersion. By good staying power, it is meant that the composition remains on the surface to which it is applied for a greater period of time than a composition not comprising fibers and at least one film-forming polymer in the form of particles in an aqueous dispersion. Compositions of this embodiment of the invention produced according to this process are particularly resistant to water and/or rubbing when applied to the skin, and effectively camouflage the skin.

In addition to the advantages mentioned above, the composition according to the invention also gives a make-up which has a fabric effect, like velvet, lace, or fur. Thus, this make-up makes it possible in particular to appear clothing-like.

The fibers which can be used in the composition of the invention can be fibers of synthetic, natural, mineral, and organic origin. They can be short or long, hollow or solid, individual or organized, such as, for example, like plaits or braids, and any combination thereof. They can be in any shape, for example, of circular or polygonal cross section, such as square, hexagonal, or octagonal, depending on the specific application envisaged. Further, their ends can be blunt and/or smooth to prevent injury.

The fibers can generally have a length in one embodiment ranging from 1 nm to 50 mm, in another embodiment ranging from 10 nm to 5 mm, and in another embodiment ranging from 0.1 mm to 1.5 mm. Their cross section can be included in one embodiment in a circle of diameter ranging from 2 nm to 1 mm, in another embodiment in a circle of diameter ranging from 20 nm to 500 mm, and in another embodiment in a circle of diameter ranging from 500 nm to 20 mm. The weight of the fibers is often given in denier or decitex.

The fibers which can be used according to the invention can be those used in the manufacture of textiles, such as, for example, silk fibers, cotton fibers, wool fibers, or flax fibers, cellulose fibers (or Rayon), such as, for example, extracted fibers such as fibers from wood, plants, or algae, polyamide (Nylon®) fibers, viscose fibers, acetate fibers, such as, for example, rayon acetate fibers, poly(p-phenyleneterephthalamide) (or aramide) fibers, such as, for example, Kevlar®, acrylic polymer fibers, such as, for example, polymethyl methacrylate or poly(2-hydroxyethyl methacrylate) fibers, polyolefin fibers, such as, for example, polyethylene or polypropylene fibers, glass fibers, silica fibers, carbon fibers, such as, for example, in graphite form, polytetrafluoroethylene fibers (such as Teflon®), insoluble collagen fibers, polyester fibers, polyvinyl chloride fibers, polyvinylidene chloride fibers, polyvinyl alcohol fibers, polyacrylonitrile fibers, chitosan fibers, polyurethane fibers, polyethylene phthalate fibers, fibers formed from a mixture of polymers such as those mentioned above, such as, for example, polyamide/polyester fibers, and mixtures of different fibers.

Moreover, the fibers can be surface-treated or untreated, and can be coated or uncoated. Coated fibers which are useful according to the invention can be, for example, polyamide fibers coated with copper sulphide for an anti-static effect, such as, for example R-STAT from Rhodia, or fibers coated with another polymer to facilitate the specific organization of the fibers (specific surface treatment), or fibers with a surface treatment which induces color and/or hologram effects, such as, for example, Lurex fiber from Sildorex.

In one embodiment, fibers of synthetic origin can be used, for example, organic fibers such as those used in surgery. For example, water-insoluble fibers can be used. The fibers which can be used according to the invention are generally polyamide, poly-p-phenylene terephthalamide, or cellulose fibers. They can generally range in length in one embodiment from 0.1 mm to 50 mm, and in another embodiment from 0.25 mm to 1.6 mm. Their cross section can be included in a circle with an average diameter generally ranging from 5 mm to 1 mm. For example, the polyamide fibers sold by the company P. Bonte under the name Polyamide 0.9 Dtex 0.3 mm, having an average diameter of 6 $\mu$m, a weight of about 0.9 decitex, and a length ranging from 0.3 mm to 1.5 mm, can be used. Poly-p-phenylene terephthalamide fibers with an average diameter of 12 $\mu$m and a length of about 1.5 mm can also be used, such as, for example, those sold under the name Kevlar Floc by the company DuPont Fibers. Cellulose (or Rayon) fibers having an average diameter of 50 $\mu$m and a length ranging from 0.5 mm to 6 mm, such as, for example, those sold under the name Natural rayon flock fiber RC1BE-N003-M04 by the company Claremont Flock can also be used. Polyethylene fibers can also be used, such as, for example, those sold under the name Shurt Stuff 13 099 F by the company Mini Fibers.

The fiber concentration depends on the specific application and on the type of product envisaged. The fibers can be present in the composition according to the invention in one embodiment in an amount generally ranging from from 0.1% to 99% by weight, relative to the total weight of the composition, in another embodiment in an amount ranging from 0.5% to 50% by weight, and in another embodiment in an amount ranging from 1% to 30% by weight.

In the present application, the expression "film-forming polymer" means a polymer which is capable, by itself or in the presence of a film-forming auxiliary agent, of forming an isolable film. The expression "polymer in the form of particles in aqueous dispersion," generally known as a latex or pseudolatex, means a phase containing water and, optionally, a compound which is soluble in water, in which the polymer is directly dispersed. This allows good cohesion and maintenance of the fibers.

Among the film-forming polymers which can be useful according to the invention are synthetic polymers, such as, for example, of the radical-mediated type or polycondensate type, and polymers of natural origin.

The expression "radical-mediated film-forming polymer" means a polymer obtained by polymerization of monomers containing unsaturation, such as ethylenic unsaturation, wherein each monomer is capable of homopolymerizing (unlike the polycondensates). The film-forming polymers of radical-mediated type can be, for example, vinyl polymers or copolymers, and, in one embodiment, are acrylic polymers.

The vinyl film-forming polymers can result from the polymerization of monomers containing ethylenic unsaturation having at least one acid group, esters of these acidic monomers, and/or amides of these acidic monomers. Anionic radical-mediated film-forming polymers are used in one embodiment, i.e., polymers having at least one monomer containing an acid group.

Monomers bearing an acid group which can be used are α,β-ethylenic unsaturated carboxylic acids such as, for example, acrylic acid, methacrylic acid, crotonic acid, maleic acid, and itaconic acid. (Meth)acrylic acid and crotonic acid can be used in one embodiment, and in another embodiment, (meth)acrylic acid can be used. The esters of acidic monomers can be chosen from the esters of (meth) acrylic acid (also known as (meth)acrylates), alkyl (meth) acrylates such as, for example, a $C_1$–$C_{20}$ alkyl in one embodiment, and a $C_1$–$C_8$ alkyl in another embodiment, aryl (meth)acrylates such as, for example, a $C_6$–$C_{10}$ aryl, and hydroxyalkyl (meth)acrylates, such as, for example, a $C_2$–$C_6$ hydroxyalkyl.

Among the alkyl (meth)acrylates which can be useful according to the invention are methyl methacrylate, ethyl methacrylate, butyl methacrylate, isobutyl methacrylate, 2-ethylhexyl methacrylate, and lauryl methacrylate. Among the hydroxyalkyl (meth)acrylates which can be useful according to the invention are hydroxyethyl acrylate, 2-hydroxypropyl acrylate, hydroxyethyl methacrylate, and 2-hydroxypropyl methacrylate. Among the aryl (meth) acrylates which can be useful according to the invention are benzyl acrylate and phenyl acrylate. The (meth)acrylic acid esters which can be used are, for example, the alkyl (meth) acrylates.

According to the present invention, the alkyl group of the esters can be either fluorinated or perfluorinated, i.e., some or all of the hydrogen atoms in the alkyl group can be replaced with fluorine atoms.

Amides of the acidic monomers which can be useful according to the invention are, for example, (meth) acrylamides such as N-alkyl(meth)acrylamides, for example, a $C_2$–$C_{12}$ alkyl. Among the N-alkyl(meth) acrylamides which can be useful according to the invention are N-ethylacrylamide, N-t-butylacrylamide, and N-t-octylacrylamide.

The vinyl film-forming polymers can also result from the homopolymerization or copolymerization of monomers chosen from vinyl esters and styrene monomers. These monomers can be polymerized with acidic monomers, esters, and/or amides thereof, such as those mentioned previously. Examples of vinyl esters which may be mentioned are vinyl acetate, vinyl neodecanoate, vinyl pivalate, vinyl benzoate, and vinyl t-butylbenzoate. Styrene monomers which may be mentioned are styrene and alpha-methylstyrene.

The list of monomers given is not intended to be limiting, and it is possible to use any monomer known to those skilled in the art which falls within the categories of acrylic monomers and vinyl monomers, including monomers modified with a silicone chain.

Acrylic film-forming polymers which can be useful according to the invention are, for example, those sold under the names Neocryl XK-90®, Neocryl A-1070®, Neocryl A-1090®, Neocryl BT-62®, Neocryl A-1079®, and Neocryl A-523® by the company Zeneca, and Dow Latex 432® by the company Dow Chemical.

Among the polycondensates which can be useful according to the invention as film-forming polymer are, for example, anionic, cationic, nonionic, and amphoteric polyurethanes, polyurethane-acrylics, polyurethane-polyvinylpyrrolidones, polyester-polyurethanes, polyether-polyurethanes, polyureas, and polyurea-polyurethanes.

The film-forming polyurethane may be chosen from, for example, aliphatic, cycloaliphatic, and aromatic polyurethanes, polyurea/urethane copolymers, and polyurea copolymers, comprising, alone or as a mixture:
- at least one sequence of aliphatic and/or cycloaliphatic and/or aromatic polyester origin,
- at least one branched or unbranched silicone sequence, such as, for example polydimethylsiloxane or polymethylphenylsiloxane, and
- at least one sequence comprising fluoro groups.

The film-forming polyurethanes as defined in the invention can also be obtained from branched or unbranched polyesters, or from alkyds comprising labile hydrogens which are modified by reaction with a diisocyanate and a difunctional organic compound such as, for example, dihydro, diamino, or hydroxyamino, wherein the alkyds further comprise either a carboxylic acid, a carboxylate group, a sulphonic acid, a sulphonate group, a neutralizable tertiary amine group, or a quaternary ammonium group.

Among the film-forming polyurethanes which can be useful according to the invention are, for example, those sold under the names Neorez R-981® and Neorez R-974® by the company Zeneca, and Avalure UR-405®, Avalure UR-410®, Sancure 875®, Sancure 2060®, Avalure UR-425®, Avalure UR-430®, Sancure 861®, Sancure 878®, and Avalure UR-450® by the company Goodrich.

Among the film-forming polycondensates which can be useful according to the invention are, for example, polyesters, polyesteramides, fatty-chain polyesters, polyamides, and epoxyester resins. The polyesters can be obtained, in a known manner, by polycondensation of dicarboxylic acids with polyols, such as, for example, diols.

The dicarboxylic acid monomers can be aliphatic, alicyclic, or aromatic. Examples of such acids which can be useful according to the invention are, for example, oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid and 2,6-naphthalenedicarboxylic acid. These dicarboxylic acidic monomers can be used alone or as a combination of at least two dicarboxylic acidic monomers. Among these monomers, the ones specifically chosen are phthalic acid, isophthalic acid, and terephthalic acid.

The diols can be chosen from aliphatic, alicyclic, and aromatic diols. The diols used are, in one embodiment, chosen from ethylene glycol, diethylene glycol, triethylene glycol, 1,3-propanediol, cyclohexanedimethanol, and 4-butanediol. Other polyols which can be useful according to the invention are, for example, glycerol, pentaerythritol, sorbitol, and trimethylolpropane.

The polyesteramides can be obtained in a similar manner to that of the polyesters, by polycondensation of diacids with diamines or with amino alcohols. Diamines which can be used are ethylenediamine, hexamethylenediamine, and meta- or para-phenylenediamine. An amino alcohol which can be used is monoethanolamine.

The polyester can also comprise at least one monomeric unit, i.e., the residue of the monomer remaining after polymer formation, bearing at least one group —$SO_3M$, wherein M represents a hydrogen atom, an ammonium ion $NH_4^+$, or a metal ion such as, for example, an $Na^+$, $Li^+$, $K^+$, $Mg^{2+}$, $Ca^{2+}$, $Cu^{2+}$, $Fe^{2+}$, or $Fe^{3+}$ ion. For example, a difunctional aromatic monomer comprising such a group —$SO_3M$ can be used.

The aromatic nucleus of the difunctional aromatic monomer also bearing a group —$SO_3M$ as described above can be chosen, for example, from benzene, naphthalene, anthracene, biphenyl, oxibiphenyl, sulphonylbiphenyl, and methylenebiphenyl nuclei. Examples of difunctional aromatic monomers also bearing a group —$SO_3M$ which can be useful according to the invention are, for example, sulphoisophthalic acid, sulphoterephthalic acid, sulphophthalic acid, and 4-sulphonaphthalene-2,7-dicarboxylic acid.

Copolymers based on isophthalate/sulphoisophthalate, such as, for example, copolymers obtained by condensation of diethylene glycol, cyclohexanedimethanol, isophthalic acid and sulphoisophthalic acid, can be useful according to the invention. Such polymers are sold, for example, under the brand name Eastman AQ by the company Eastman Chemical Products.

The optionally modified polymers of natural origin can be chosen, for example, from shellac resin, sandarac gum, dammar resins, elemi gums, copal resins, and water-insoluble cellulose polymers.

Mention may also be made of the polymers resulting from the radical polymerization of one or more radical-mediated polymers inside and/or partially at the surface of pre-existing particles of at least one polymer chosen from polyurethanes, polyureas, polyesters, polyesteramides, and/or alkyds. These polymers are generally referred to as hybrid polymers.

The film-forming polymer used is one which is capable of forming a film which satisfies, under the measurement conditions defined before the examples, at least one of the following physicochemical conditions:
- a Young's modulus of less than about 200 MPa in one embodiment, less than about 100 MPa in another embodiment, and less than 80 MPa in another embodiment,
- an elongation of greater than about 200% in one embodiment, and greater than 300% in another embodiment, or
- a hardness of less than 110 seconds in one embodiment, less than 70 seconds in another embodiment, and less than 55 seconds in another embodiment.

The dispersion comprising at least one film-forming polymer can be prepared according to the known methods by a person skilled in the art, on the basis of his or her general knowledge.

The size of the polymer particles in aqueous dispersion can generally range from 10 nm to 500 nm in one embodiment, and from 20 nm to 300 nm in another embodiment.

The polymer in aqueous dispersion can be present in the composition according to the invention in an amount generally ranging, in one embodiment, from 1% to 50% by weight of film-forming polymer solids, relative to the total weight of the composition, and ranging from 5% to 40% by weight in another embodiment.

The composition according to the invention can comprise an auxiliary film-forming agent which promotes the formation of a film with the particles of the film-forming polymer. Such a film-forming agent can be chosen from any compound known to those skilled in the art as being capable of satisfying the desired function, such as, for example, plasticizers and coalescers.

The medium for the composition of the invention is aqueous in one embodiment of the invention. The water content in the composition can generally range, in one embodiment, from 1% to 70% by weight, relative to the total weight of the composition, and from 1% to 50% by weight in another embodiment.

The composition may contain at least one thickener for adjusting the viscosity in order to improve application. The thickeners which can be used according to the invention can be chosen from:
- water-soluble cellulose thickeners such as, for example, hydroxyethylcellulose, methylcellulose, hydroxypropylcellulose, and carboxymethylcellulose, such as, for example, the gums sold under the name "Cellosize QP 4001H" by the company Amercol;
- guar gum, such as, for example, those sold under the name "Vidogum GH 175" by the company Unipectine and under the name "Jaguar C" by the company Meyhall;

the quaternized guar gum sold under the name "Jaguar C-13-S" by the company Meyhall;

nonionic guar gums comprising $C_1$–$C_6$ hydroxyalkyl groups, such as, for example, hydroxymethyl, hydroxyethyl, hydroxypropyl, and hydroxybutyl groups, such as, for example, those sold under the names "Jaguar HP8," "Jaguar HP60," "Jaguar HP120," "Jaguar DC 293," and "Jaguar HP 105" by the company Meyhall, or under the name "Galactasol 4H4FD2" by the company Aqualon;

xantham gums, carob gums, scleroglucan gums, gellan gums, rhamsan gums, and karaya gums;

alginates, maltodextrin, starch and its derivatives, hyaluronic acid and its salts;

clays, such as, for example, montmorillonites, hectorites and laponites;

crosslinked polyacrylic acids such as the "Carbopol" products from the company Goodrich;

the polyglyceryl (meth)acrylate polymers sold under the names "Hispagel" or "Lubragel" by the companies Hispano Quimica or Guardian;

polyvinylpyrrolidone;

polyvinyl alcohol;

crosslinked acrylamide polymers and copolymers, such as, for example, those sold under the names "PAS 5161" or "Bozepol C" by the company Hoechst, or "Sepigel 305" by the company Seppic;

the crosslinked methacryloyloxyethyltrimethylammonium chloride homopolymers sold under the name "Salcare SC95" by the company Allied Colloid; and associative polymers, such as, for example, associative polyurethanes.

According to the invention, the thickener is preferably chosen from associative polyurethanes. Associative polyurethanes are nonionic block copolymers comprising in the chain both hydrophilic sequences, usually of polyoxyethylenated nature, and hydrophobic sequences, which may be aliphatic chain units alone and/or cycloaliphatic and/or aromatic chain units.

In one embodiment, these polymers comprise at least two hydrocarbon-based lipophilic chains containing from 6 to 30 carbon atoms, separated by a hydrophilic sequence. The hydrocarbon-based chains can be pendant chains or chains at the end of the hydrophilic sequence. It is possible for one or more pendant chains to be present. In addition, the polymer can comprise a hydrocarbon-based chain at one or both ends of a hydrophilic sequence.

The polymers can be sequenced in triblock or multiblock form. Hydrophobic sequences can thus be at each end of the chain, such as, for example, a triblock copolymer with a hydrophilic central sequence, or distributed both at the ends and in the middle of the chain, such as, for example, a multiblock copolymer. The polymers can also be graft polymers or starburst polymers. In one embodiment, the polymers can be triblock copolymers whose hydrophilic sequence is a polyoxyethylenated chain comprising from 50 to 1000 oxyethylene groups. In general, the associative polyurethanes comprise a urethane linkage between the hydrophilic sequences, which explains the origin of the name. Likewise, polymers whose hydrophilic sequences are linked by chemical linkages other than a polyurethane linkage to the lipophilic sequences are also featured among the associative polyurethanes.

As examples of associative polymers which can be used in the invention, mention may be made of the polymer $C_{16}$-$OE_{120}$-$C_{16}$ sold by the company Hüls under the name "Serad FX1100," which contains a urethane function and has a weight-average molecular weight of 1300. In this polymer, OE is an oxyethylene unit. Associative polymers which can also be used according to the invention are, for example, "Rheolate 205," which contains a urea function, sold by the company Rheox, or "Rheolate 208" or "Rheolate 204." These associative polyurethanes are sold in pure form. The product "DW 1206B" from Rhom & Haas, containing a $C_{20}$ alkyl chain and a urethane linkage, which is sold at a concentration of 20% solids in water, can also be used.

Solutions or dispersions of these polymers, such as in aqueous or aqueous-alcoholic medium, can also be used. Examples of such polymers which can be useful according to the invention are, for example, "Serad FX1010," "Serad FX1035," and "Serad FX1070" sold by the company Hüls, and "Rheolate 255," "Rheolate 278," and "Rheolate 244" sold by the company Rheox. The products "DW 1206F" and "DW 1206J" can also be used, as can "Acrysol RM 184" and "Acrysol 44" (also known as "Aculyn 44") from the company Rhom & Haas, and "Borchigel LW 44" from the company Borchers.

The associative polymers which can be used in the invention are, for example, those described in the article by G. Fonnum, J. Bakke, and Fk. Hansen, *Colloid Polym. Sci.* 271, 380–389 (1993), the disclosure of which is incorporated by reference herein.

In the composition according to the invention, the at least one thickener can be present in an amount ranging, in one embodiment, from 0.1% to 20% by weight, relative to the total weight of the composition, and from 1% to 10% by weight in another embodiment.

To promote rapid drying of the composition after it has been applied to the skin and/or superficial body growths, the composition can comprise drying accelerators such as, for example, volatile solvents, for example, water-miscible volatile organic solvents such as ethanol. The amount of such organic solvent is chosen such that the viscosity of the composition is maintained well within the range defined above. These organic solvents can be present in the composition in one embodiment in an amount ranging up to 15% by weight, relative to the total weight of the composition, ranging from 0.1% to 15% in another embodiment, ranging up to 10% by weight in another embodiment, and ranging from 0.5% to 10% in yet another embodiment. The term "volatile" means a compound which is capable of evaporating on contact with the skin, at room temperature.

The composition can also comprise other ingredients commonly used in cosmetics, such as, for example, plasticizers, coalescers, fillers, dyestuffs such as, for example, pigments or dyes, waxes, surfactants, preserving agents, oils, moisturizers, and fragrances. Needless to say, a person skilled in the art will take care to select this or these optional additives, and/or the amount thereof, such that the advantageous properties of the three-dimensional deposit on the skin and/or superficial body growths are not, or not substantially, adversely affected.

The composition can be applied to the skin with the aid of any applicator known to those skilled in the art, such as, for example, brushes, applicators with a foam tip, a flocked pen, felt-tipped applicators, fine brushes, and spatulas.

The composition according to the invention can also be applied to the skin with the aid of a stencil. The composition thus deposited in the empty parts of the stencil keeps its shape after the stencil has been removed, thus giving a highly decorative make-up on the skin.

The invention is illustrated in greater detail in the non-limiting example which follows.

EXAMPLE

A. Measurement of the Elongation

The elongation of the film obtained was measured according to the ASTM Standards, Volume 06.01, Standard D 2370-92 "Standard Test Method for Tensile Properties of Organic Coatings."

B. Measurement of the Hardness

The hardness of the film was measured according to ASTM Standard D-43-66, or Standard NF-T 30-016 (October 1981), using a Persoz pendulum. The film deposited on the support should have a thickness of about 300 microns before drying. After drying for 24 hours at 30° C. and at a relative humidity of 50%, a film with a thickness of about 100 microns was obtained. Its hardness was then measured at 30° C. and 50% relative humidity.

C. Measurement of the Young's Modulus (or modulus of elasticity)

The Young's modulus (modulus of elasticity) was measured according to ASTM Standards, Volume 06.01, Standard D 2370-92 "Standard Test Method for Tensile Properties of Organic Coatings". The film deposited on the support should have a thickness of about 300 microns before drying. After drying for 7 days at 21° C. and at a relative humidity of 50%, a film with a thickness of about 100 microns was obtained.

The samples measured were 5 mm wide and 100 microns thick. The distance between the jaws was 25 mm. The tensile speed was 1000 mm per minute.

Example

A make-up composition for the skin comprising the ingredients below was prepared, by simple mixing the following at room temperature:

| | |
|---|---|
| Aqueous dispersion of polyester-polyurethane (49% solids) (Avalure UR-425 from the company Goodrich) | 12 g AM |
| Polyethylene fibers (Short Stuff 13038F from the company Mini Fibers) | 7 g |
| Dye | q.s. |
| Preserving agents | q.s. |
| Water | q.s. 100 g |

This composition adhered well to the skin and gave make-up which had the appearance of a fabric. The fibers were well maintained in the polymer film, and the make-up showed good resistance to water and to rubbing.

What is claimed is:

1. A process for making up or caring for the skin, comprising applying to the skin a cosmetic composition comprising, in a physiologically acceptable medium, fibers and at least one film-forming polymer in the form of particles in aqueous dispersion.

2. A process according to claim 1, wherein the fibers are chosen from silk fibers, cotton fibers, wool fibers, flax fibers, cellulose fibers, polyamide fibers, viscose fibers, acetate fibers, poly(p-phenyleneterephthalamide) fibers, acrylic polymer fibers, polyolefin fibers, glass fibers, silica fibers, carbon fibers, polytetrafluoroethylene fibers, insoluble collagen fibers, polyester fibers, polyvinyl chloride fibers, polyvinylidene chloride fibers, polyvinyl alcohol fibers, polyacrylonitrile fibers, chitosan fibers, polyurethane fibers, polyethylene phthalate fibers, fibers formed from mixtures of these polymers, and mixtures thereof.

3. A process according to claim 1, wherein the fibers are fibers of synthetic origin.

4. A process according to claim 1, wherein the fibers have a length ranging from 1 nm to 50 mm.

5. A process according to claim 4, wherein the fibers have a length ranging from 10 nm to 5 mm.

6. A process according to claim 1, wherein the fibers have a circular or polygonal cross section.

7. A process according to claim 1, wherein the fibers have a cross section which is included in a circle of diameter ranging from 5 mm to 1 mm.

8. A process according to claim 1, wherein the fibers are present in an amount ranging from 0.1% to 99% by weight, relative to the total weight of the composition.

9. A process according to claim 8, wherein the fibers are present in an amount ranging from 0.5% to 50% by weight, relative to the total weight of the composition.

10. A process according to claim 9, wherein the fibers are present in an amount ranging from 1% to 30% by weight, relative to the total weight of the composition.

11. A process according to claim 1, wherein the at least one film-forming polymer is chosen from synthetic polymers and polymers of natural origin.

12. A process according to claim 11, wherein the synthetic polymers are chosen from radical-mediated polymers and polycondensates.

13. A process according to claim 12, wherein the radical-mediated polymers are chosen from vinyl polymers resulting from the polymerization of at least one monomer chosen from α,β-ethylenic unsaturated carboxylic acids, esters of α,β-ethylenic unsaturated carboxylic acids, amides of α,β-ethylenic unsaturated carboxylic acids, vinyl esters, and styrene monomers.

14. A process according to claim 12, wherein the polycondensates are chosen from polyurethanes, polyesters, polyesteramides, polyamides, and epoxyester resins.

15. A process according to claim 11, wherein the polymers of natural origin are chosen from shellac resin, sandarac gum, dammar resins, elemis gums, copal resins, and water-insoluble cellulose polymers.

16. A process according to claim 1, wherein the at least one film-forming polymer is capable of forming a film which satisfies at least one of the following physicochemical conditions:

a) a Young's modulus of less than about 200 MPa, b) an elongation of greater than about 200%, or c) a hardness of less than 110 seconds.

17. A process according to claim 1, wherein the at least one film-forming polymer is present in an amount ranging from 1% to 50% by weight of solids, relative to the total weight of the composition.

18. A process according to claim 17, wherein the at least one film-forming polymer is present in an amount ranging from 5% to 40% by weight of solids, relative to the total weight of the composition.

19. A process according to claim 1, wherein the composition further comprises at least one additive chosen from thickeners, plasticizers, coalescers, fillers, dyestuffs, waxes, surfactants, preserving agents, oils, moisturizers, and fragrances.

20. A process according to claim 1, wherein the composition is applied to the skin with the aid of a stencil.

21. A process according to claim 1, wherein the composition further comprises at least one auxiliary film-forming polymer.

22. A process according to claim 1, wherein the composition further comprises water.

23. A process according to claim 22, wherein the water is present in an amount ranging from 1% to 70% by weight, relative to the total weight of the composition.

24. A process according to claim 1, wherein the composition further comprises a drying accelerator.

25. A cosmetic composition comprising, in a physiologically acceptable medium, fibers and at least one film-forming polymer in the form of particles in aqueous dispersion, wherein the at least one film-forming polymer is chosen from polyurethanes.

26. A cosmetic composition according to claim 25, wherein the fibers are chosen from silk fibers, cotton fibers, wool fibers, flax fibers, cellulose fibers, polyamide fibers, viscose fibers, acetate fibers, poly(p-phenyleneterephthalamide) fibers, acrylic polymer fibers, polyolefin fibers, glass fibers, silica fibers, carbon fibers, polytetrafluoroethylene fibers, insoluble collagen fibers, polyester fibers, polyvinyl chloride fibers, polyvinylidene chloride fibers, polyvinyl alcohol fibers, polyacrylonitrile fibers, chitosan fibers, polyurethane fibers, polyethylene phthalate fibers, fibers formed from mixtures of these polymers, and mixtures thereof.

27. A cosmetic composition according to claim 25, wherein the fibers are fibers of synthetic origin.

28. A cosmetic composition according to claim 25, wherein the fibers have a length ranging from 1 nm to 50 mm.

29. A cosmetic composition according to claim 28, wherein the fibers have a length ranging from 10 nm to 5 mm.

30. A cosmetic composition according to claim 25, wherein the fibers have a circular or polygonal cross section.

31. A cosmetic composition according to claim 25, wherein the fibers have a cross section included in a circle with an average diameter ranging from 5 mm to 1 mm.

32. A cosmetic composition according to claim 25, wherein the fibers are present in an amount ranging from 0.1% to 99% by weight, relative to the total weight of the composition.

33. A cosmetic composition according to claim 32, wherein the fibers are present in an amount ranging from 0.5% to 50% by weight, relative to the total weight of the composition.

34. A cosmetic composition according to claim 33, wherein the fibers are present in an amount ranging from 1% to 30% by weight, relative to the total weight of the composition.

35. A cosmetic composition according to claim 25, wherein the polyurethanes are chosen from polyester-polyurethanes and polyether-polyurethanes.

36. A cosmetic composition according to claim 25, wherein the polyurethanes are anionic.

37. A cosmetic composition according to claim 25, wherein the at least one film-forming polymer is capable of forming a film which satisfies at least one of the following physicochemical conditions:

a) a Young's modulus of less than about 200 MPa, b) an elongation of greater than about 200%, or c) a hardness of less than 110 seconds.

38. A cosmetic composition according to claim 25, wherein the at least one film-forming polymer is present in a solids content ranging from 1% to 50% by weight, relative to the total weight of the composition.

39. A cosmetic composition according to claim 38, wherein the at least one film-forming polymer is present in a solids content ranging from 5% to 40% by weight, relative to the total weight of the composition.

40. A cosmetic composition according to claim 25, wherein the composition further comprises at least one additive chosen from thickeners, plasticizers, coalescers, fillers, dyestuffs, waxes, surfactants, preserving agents, oils, moisturizers, and fragrances.

41. A process for improving the staying power of a skin make-up composition, comprising adding to the skin make-up composition fibers and at least one film-forming polymer in the form of particles in aqueous dispersion.

42. A process according to claim 41, wherein the at least one film-forming polymer is chosen from polyurethanes.

43. A process for camouflaging the skin or skin imperfections, comprising applying to the skin or skin imperfections a cosmetic composition comprising, in a physiologically acceptable medium, fibers and at least one film-forming polymer in the form of particles in aqueous dispersion.

44. A cosmetic composition comprising, in a physiologically acceptable medium, an amount of fibers effective to camouflage the skin, and at least one film-forming polymer in the form of particles in an aqueous dispersion.

45. A cosmetic composition according to claim 44, wherein the at least one film-forming polymer is chosen from polyurethanes.

* * * * *